United States Patent [19]
Sanfilippo, II

[11] Patent Number: 5,919,160
[45] Date of Patent: Jul. 6, 1999

[54] VASCULAR ACCESS DEVICE AND METHOD OF INSTALLING SAME

[76] Inventor: Dominic Joseph Sanfilippo, II, 9157-28th St., Ada, Mich. 49301

[21] Appl. No.: 08/728,825

[22] Filed: Oct. 10, 1996

[51] Int. Cl.[6] .................................................. A61M 11/00
[52] U.S. Cl. .............................. 604/93; 604/19; 604/502; 604/891.1
[58] Field of Search ................................... 604/19, 27, 48, 604/93, 51, 52, 175, 267, 165, 891.1, 124; 128/DIG. 12

[56] References Cited

U.S. PATENT DOCUMENTS

| | | | |
|---|---|---|---|
| Re. 31,855 | 3/1985 | Osborne | 604/161 |
| 4,710,167 | 12/1987 | Lazorthes | 604/93 |
| 4,767,410 | 8/1988 | Moden et al. | 604/175 |
| 4,776,839 | 10/1988 | Doumenis | 604/9 |
| 4,826,480 | 5/1989 | Diaz et al. | 604/49 |
| 4,840,190 | 6/1989 | Sasaki | 128/897 |
| 5,085,644 | 2/1992 | Watson et al. | 604/153 |
| 5,167,638 | 12/1992 | Felix et al. | 604/175 |
| 5,261,885 | 11/1993 | Lui | 604/247 |
| 5,281,205 | 1/1994 | McPherson | 604/267 |
| 5,360,407 | 11/1994 | Leonard | 604/175 |
| 5,484,409 | 1/1996 | Atkinson et al. | 604/96 |
| 5,562,617 | 10/1996 | Finch, Jr. et al. | 604/93 |

OTHER PUBLICATIONS

Product Brochure entitled *Vital–Port Vascular Access Sets* by Cook Incorporated, Copyright Cook Incorporated 1995.

*Primary Examiner*—Corrine McDermott
*Assistant Examiner*—Cris L. Rodriguez
*Attorney, Agent, or Firm*—Van Dyke, Gardner, Linn & Burkhart, LLP

[57] ABSTRACT

A vascular access device is provided which can be used for chronic venous or organ access. When implanted, the device facilitates repeated intermittent infusions of medical treatment while reducing the risk of infection at the implant site. The vascular access device comprises an elongated body and a delivery tube coupled to the elongated body for delivering the medical treatment to a preselected site in a patient's body, which permits subcutaneous implanting of the device with a minimally invasive procedure. A sheath and a dilator are adapted to form an access tunnel in the patient's body commensurate in configuration with the elongated body of the device. A guide wire is provided to guide the sheath and dilator from a first opening to a second opening in the patient's body. The introduction of the sheath eases the placement of the device and reduces access site trauma to the vein, organ, or any other location in the body to which the medicine or therapy is to be applied. Once implanted, the delivery tube of the device cooperates with another sheath, which is inserted and guided along another guide wire that extends to the preselected site in the patient's body. Furthermore, a retrieval tool is provided which cooperates with the elongated body of the device for removal of the device from the body.

37 Claims, 6 Drawing Sheets

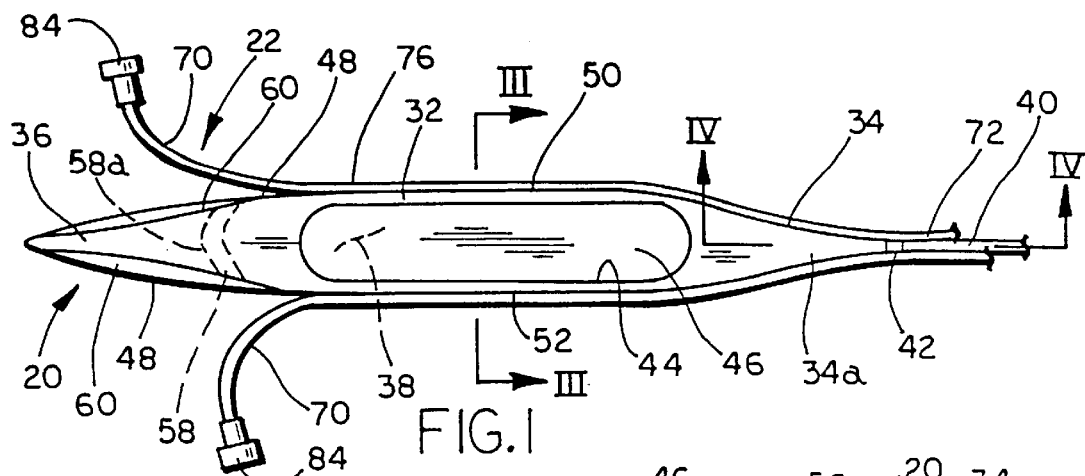
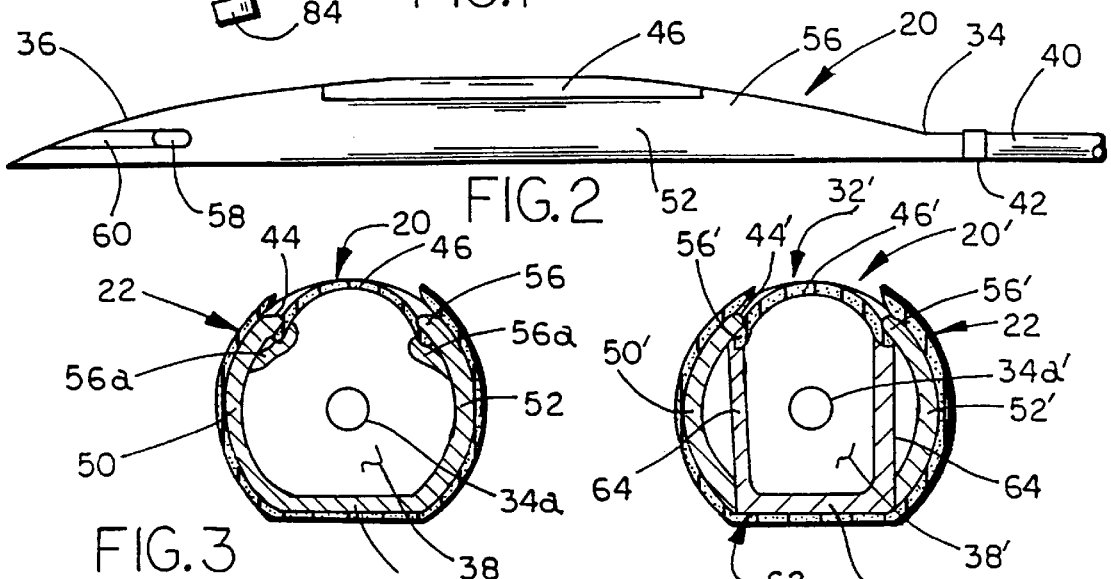
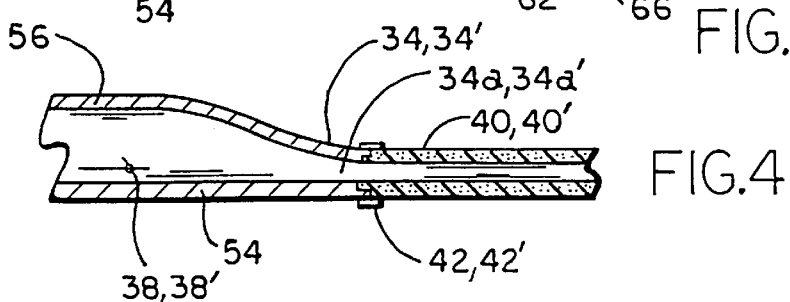
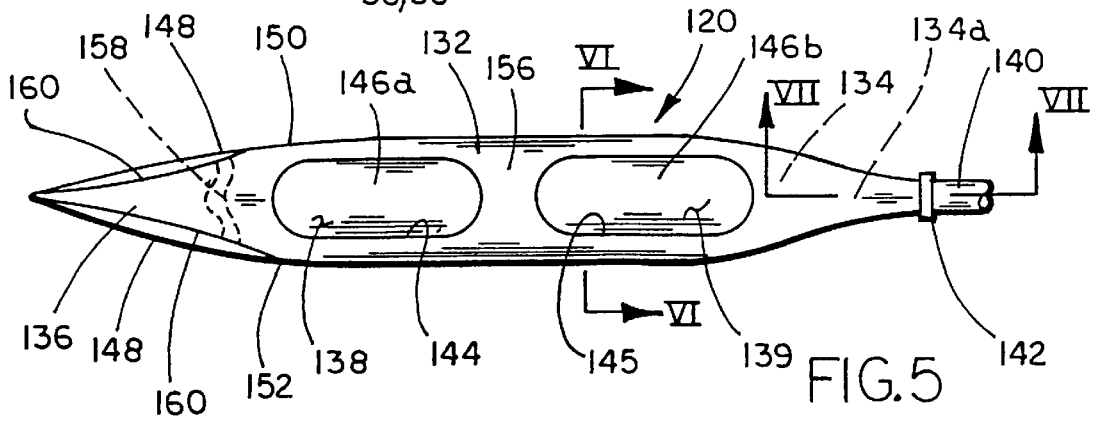

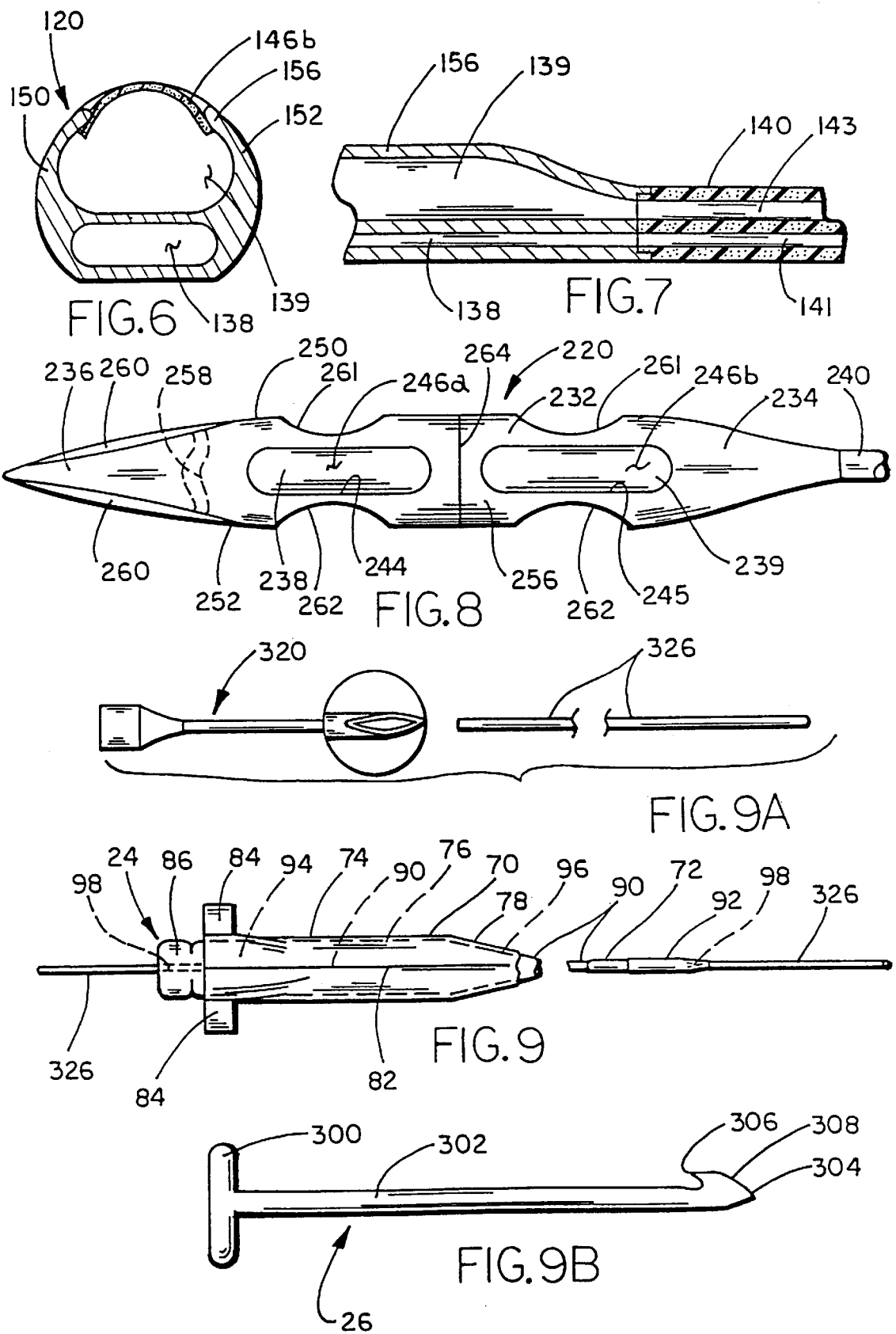

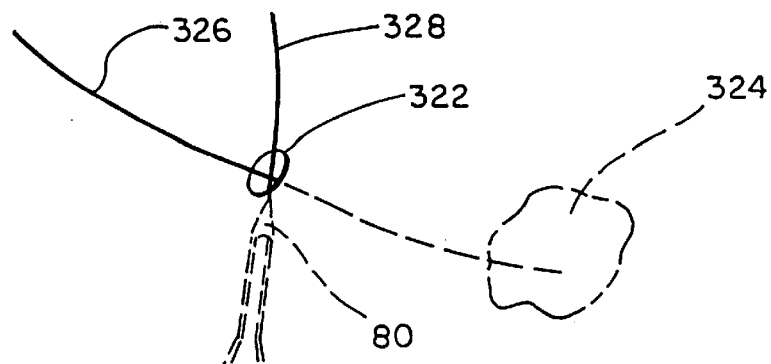
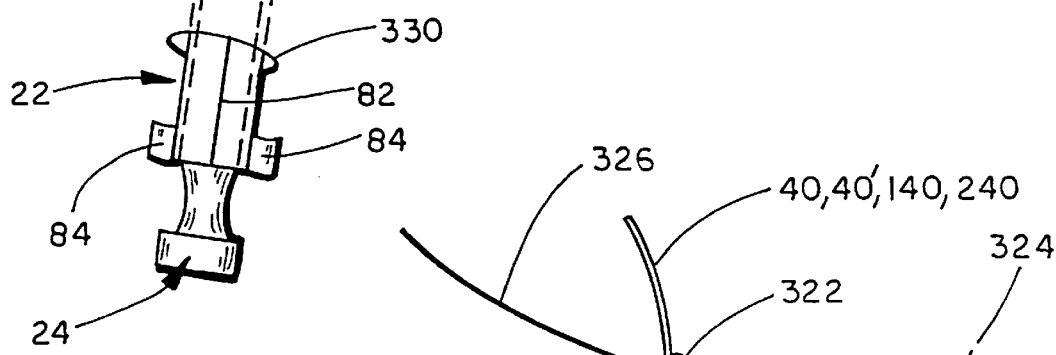
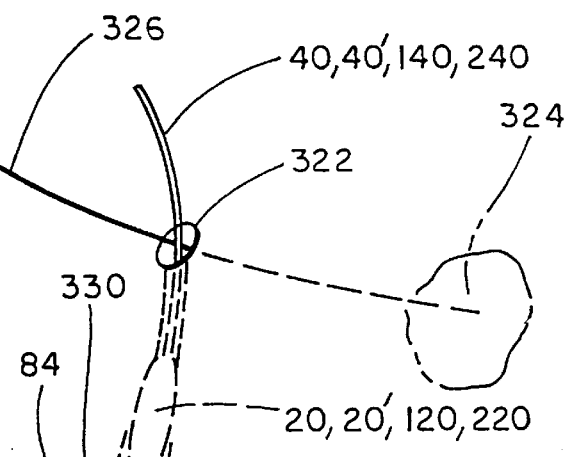
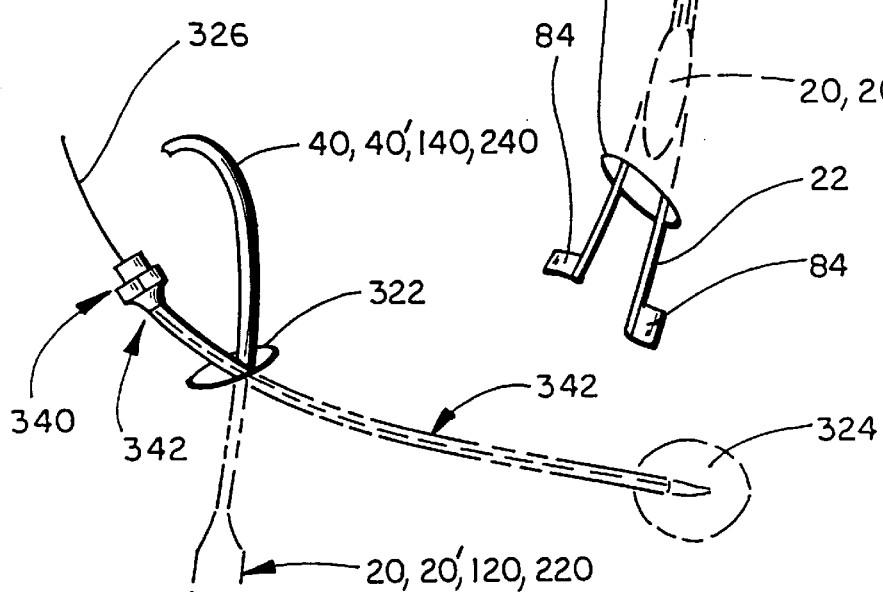
FIG. 12
FIG. 13
FIG. 14

VASCULAR ACCESS DEVICE AND METHOD OF INSTALLING SAME

TECHNICAL FIELD AND BACKGROUND OF THE INVENTION

This invention relates to vascular access systems implanted in individuals for the infusion of medication and the like, and particularly to vascular access systems which permit repeated introduction of medication into the device with minimal tissue damage to the individual.

In the treatment of many illnesses, it is necessary to repeatedly infuse medication directly into the bloodstream, into a particular organ, or otherwise to a particular medication site. For example, various chemotherapy regimes for treatment of cancerous conditions require frequent periodic medication. Bowel diseases and bone infections are other examples of conditions which require repeated treatment, as does the periodic dispensing of pain medication for terminally ill patients. In such frequent medication situations, to avoid having to locate a blood vessel for injection by needle each time, it is preferred to implant a catheter into the circulatory system through which the medication can be infused. Likewise, catheters are implanted to dispense medication directly to diseased or other treatment sites. Often, the medication is toxic in concentrated amounts and, therefore, must be infused through a catheter into a large volume of blood. To accomplish this, the catheter is fed through a vessel to a large vein or a chamber of the heart.

A problem that arises with some implanted vascular access systems is that, despite steps taken after they are used to keep them clean, the catheter may become infected. Given sufficient time, any catheter system which leaves the access opening external of the body will necessarily develop infection at the site where the catheter passes through the skin. While fully implanting a catheter device may reduce the problem of infection, other devices which are fully implanted require more invasive surgery, resulting in more discomfort, greater expense, and a longer recovery period. Moreover, these invasive techniques tend to form unsightly scars and scar tissue.

Various removable devices have been developed to administer medications to the large veins in the body or to a chamber in the heart, including external extending catheters, such as those referred to as BROVIAC, GROSHONG, and HICKMAN catheters. While there are differences between these external extending catheters, in the medical trade these various catheters are generally collectively referred to as BROVIAC-type catheters, or "BROVIACS." Another general type of system which is wholly implanted is generally referred to as a vascular port, such as, for example, PORT-A-CATH®, available from Pharmacia Deltec, Inc., in St. Paul, Minn., or as disclosed in U.S. Pat. No. 5,281,205 to McPherson, or VITAL-PORT® available from Cook Inc. in Bloomington, Ind.

The externally extending catheters are implanted using a guide wire, which is inserted into the body and directed to the point of application through the cannula of a large needle. Once the guide wire is in place in the body, a sheath is fitted on a dilator and guided down the guide wire by the dilator. When the dilator is withdrawn, the sheath forms a tunnel through the body to the point of application. The distal end of the catheter is then directed to the point of application through the sheath, leaving the proximate end of the catheter extending from the body. The sheath is formed from peel away sections, which are separated to remove the sheath and leave the catheter extending into the body to the selected treatment site.

Another prior art technique is referred to as a direct cutdown technique, in which an incision is made over the vein and the catheter is then inserted directly into the vein without use of a guide wire. The tunnel may be formed using a second cutdown or skin incision and a sharp tipped hollow metal trocar tunneling device.

An advantage of the externally extending catheters is that they can be inserted under light anesthesia on an outpatient basis. Furthermore, they tend to require less invasive procedures, requiring only a small incision in the skin. Moreover, the procedure is relatively quick. An external extending catheter can be implanted or removed in a matter of fifteen minutes or thereabouts. Moreover, the externally extending catheter can be used for numerous applications, such as chemotherapy, treatment of bowel disease, blood product infusions, bone infection, and can be used to administer pain medicines for terminally ill or seriously injured persons. However, the disadvantages of the externally extending catheter include a significant likelihood of infection at the point of exit from the body, an unsightly and somewhat intimidating medical device protruding from the body, and a restriction on the patient's activities. The patient cannot swim or engage in numerous other activities that would expose the catheter exit site to an even greater risk of infection.

Vascular ports eliminate some of the disadvantages of the externally extending catheters. Vascular ports are implanted beneath the skin and, therefore, eliminate some of the risk of infection. Furthermore, the patient is generally able to engage in most activities, including swimming. However, vascular access ports require a more invasive surgical procedure in order to implant or remove the port in or from the body. Conventional vascular ports require that a large incision be made in the skin and a cavity physically excavated below the skin to receive the port device. Moreover, the port is typically sutured to the muscle fascia. Once the port is in place and the delivery tubing is inserted and directed to the site of application, the incision is closed, leaving a relatively large scar site and protrusion of the skin at the port location. The medication is delivered to the port transdermally by a needle, which is pushed through the skin and into the chamber of the port through a membrane of material such as silicone. The disadvantage of the port is that it requires an invasive and more time consuming surgical procedure. Therefore, the procedure is, in general, significantly more expensive than the implanting of conventional externally extending catheters. Furthermore, when the port gets infected, the infection tends to be a large infection and requires similarly invasive procedures for removal of the vascular port.

SUMMARY OF THE INVENTION

Accordingly, the present invention provides a new and unique vascular access device, as well as method and apparatus for implanting and removing the vascular access device, which provides a venous and arterial implantable access system designed to permit repeated access to the vascular system for the parenteral delivery of medications, nutritional solutions, and other fluids to selected sites within the vascular system and for sampling of venous blood.

According to one aspect of the invention, a vascular access device includes an elongated implant body having at least one access chamber for receiving medical treatment. A first opening is provided in a first end of the elongated implant body in communication with the access chamber. A second access opening is provided in a wall of the elongated implant body, also in communication with the access chamber. A tubular member is connected to the first end of the elongated body and has at least one passageway that is in communication through the first opening with the access chamber for delivering medical treatment from the access chamber to a preselected treatment site in the body of a patient. A membrane is provided which covers the second access opening; and is adapted to receive a percutaneous needle puncture without leakage from the puncture.

In one aspect, the leading first end of the elongated implant body is generally pointed in order to ease insertion of the vascular access device into an opening in the body of the patient. In another aspect, the opposite second end of the vascular access device body is generally pointed to ease removal of the elongated implant body from the patient. In further aspect, the second end of the elongated implant body includes an aperture that receives a hook of a retrieval device. In other preferred aspects, the elongated implant body provides an access opening to the access chamber that is elongated longitudinally with the implant body, tactile identification structures in registry with the access opening of the implant body facilitate locating the access opening once implanted, and two separate access chambers with a tactile differentiation structure permit two separate access; openings to be located and distinguished after implanting.

According to another aspect of the invention, a vascular access kit includes a vascular access device as described above and a novel sheath and dilator for insertion of the vascular access device. The dilator includes a proximate end portion of the shaft adjacent the handle with an enlarged cross-section lobe, which lobe preferably tapers down to the smaller cross-section of the remaining dilator shaft. A coextensive passageway through the dilator from the handle to the distal end of the shaft passes a guide wire therethrough. The distal end portion of the dilator shaft is adapted for inserting a tear-away sheath into an opening in the body of the patient. The sheath includes a tubular body that, likewise, includes an enlarged diameter enclosure proximate the open end which mates with the enlarged lobe of the dilator. The dilator is used to force the enlarged sheath enclosure into the patient, which enlarged sheath enclosure then accommodates the elongated implant body. The tear-away sheath may be removed, leaving the elongated implant body wholly implanted within the patient.

In yet another aspect of the invention, a novel retrieval device is used in the removal of the vascular access device. The retrieval device includes a handle and a shaft extending from the handle. The shaft includes a hooked distal end for engaging a retrieval aperture in the second end of the elongated body of the vascular access device. Preferably, the retrieval device has a generally pointed end to ease insertion, as well as a guide edge for guiding the hook along grooves in the implant body toward the retrieval aperture.

In other aspects, the kit further includes a multiple needle assembly. The needle assembly includes a mounting body that holds at least two needles in proper registry to simultaneously access two spaced access openings on the elongated implant body. A pair of tubes is coupled to the needles. In one preferred aspect, the noncoring needles extend generally orthogonally from the respective tubes, while in another preferred aspect, the noncoring needles form acute angles with respect to the respective tubes, most preferably at angles of approximately 30 degrees.

According to yet another aspect of the invention, a method of inserting a vascular access device in the body of a patient includes the steps of inserting a guide wire into a body access hole at one location in the body of a patient and extending the guide wire to a desired location in the body. A tunnel guide wire is inserted either into the body access hole and exited from the body through a tunnel hole at another location on the body or vice versa. A sheath and dilator of the present invention are guided into the tunnel opening along the tunnel guide wire until the distal end of the sheath is protruded externally from the body through the body access hole at the first location. The tunnel guide wire and dilator are removed from the body. The vascular access device of the present invention is inserted into the open proximate end of the sheath and extended such that the delivery tube of the vascular access device protrudes exteriorly of the body from the first location. Another body access sheath is inserted along the body access guide wire using a dilator and guided to the desired location in the body. The body access guide wire and dilator are removed from the body, leaving the body access sheath in place. The protruding delivery tube of the vascular access device is guided down the body access sheath to the desired location in the body, and the sheath is then removed. Any bridging part of the delivery tube which protrudes from the first opening is inserted through the opening.

In this manner, the vascular access device is completely subcutaneously implanted in the body. These and other advantages, benefits, and objects will be understood by one skilled in the art from the drawings, description, and claims which follow.

DESCRIPTION OF THE DRAWINGS

FIG. 1 is an enlarged view of the vascular access device being inserted into the sheath of the present invention;

FIG. 2 is a side elevational view of the vascular access device illustrating a transverse aperture formed in the vascular device body;

FIG. 3 is a cross-sectional view taken along line III—III of FIG. 1;

FIG. 3A is a view similar to FIG. 3 illustrating an alternate method of assembling the vascular access device of the present invention;

FIG. 4 is a cross-sectional view taken along line IV—IV of FIG. 1;

FIG. 5 is a plan view of a second embodiment of the vascular access device of the present invention having a pair of lumens;

FIG. 6 is a cross-sectional view taken along line VI—VI of FIG. 5;

FIG. 7 is a cross-sectional view taken along line VII—VII of FIG. 5;

FIG. 8 is a plan view of a third embodiment of the vascular access device of the present invention;

FIG. 9 is an enlarged partial cut-away view of the dilator and sheath being guided along the second guide wire of the present invention;

FIG. 9A is an enlarged view of an introducer needle and guide wire;

FIG. 9B is an enlarged view of the retrieval tool of the present invention;

FIG. 12 is a perspective view of a dilator and sheath of the present invention being guided along the second guide wire;

FIG. 13 is a perspective view of a vascular access device being inserted into the sheath of the present invention having the delivery tube of the vascular access device extending exteriorly of the body from the first location;

FIG. 14 is a plan view of a conventional dilator and sheath being inserted into the body and guided along the first guide wire;

DETAILED DESCRIPTION OF THE PREFERRED EMBODIMENTS

Figure 9C:
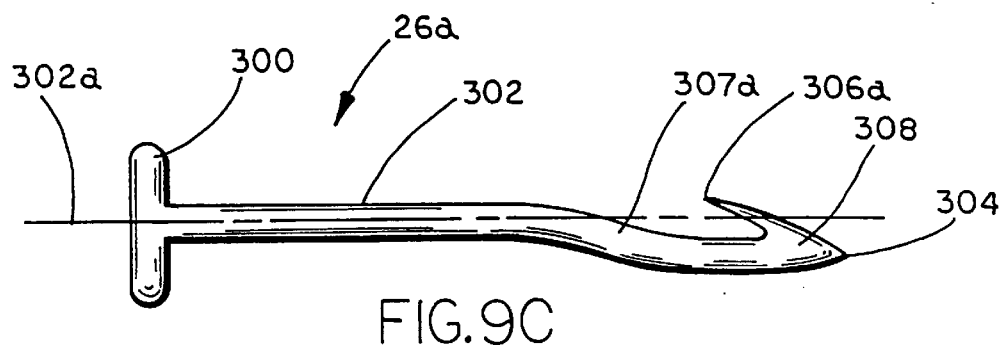
FIG. 9C is an enlarged view of another embodiment of the retrieval tool.

The invention is embodied in a unique vascular access device, a preferred form of which is shown generally at FIG. 1 and referenced by numeral 20. Vascular access device 20 is implanted by a unique implant procedure that may be quickly performed on an outpatient basis. A unique tear-away sheath 22 is used in the implanting procedure, during which sheath 22 is implanted through a narrow opening or incision in the patient through use of a unique dilator 24 (FIG. 9). In the event that removal of vascular access device 20 is required, a unique retrieval tool or device 26 (FIG. 9B) is used to facilitate the removal, again through a narrow incision in the patient.

As best seen in FIG. 1, vascular access device 20 includes an elongated implant body 32 having a first end 34 and a second end 36. At least one access chamber 38 is formed within elongated implant body 32 so as to provide a fluid impermeable chamber for receiving a treatment fluid. First end 34 of elongated implant body 32 includes an outlet aperture 34a, which is in communication with access chamber 38. First end 34 is further connected to a delivery tube 40. Delivery tube 40 may be coupled to elongated implant body 32 by known means, such as by a clamp 42, an appropriate adhesive agent, or the like. Delivery tube 40 is preferably a silicone catheter and includes a lumen extending therethrough in fluid communication with the opening 34a in first end 34, so that the fluid in access chamber 38 may be delivered by delivery tube 40 to the appropriate vein, organ, or other preselected treatment site within the body of the patient.

Elongated implant body 32 further includes an elongated access opening 44 formed in a wall of elongated implant body 32. Elongated access opening 44 extends longitudinally relative to elongated implant body 32, and is covered and sealed by a selectively permeable closure membrane 46. Although closure membrane 46 is fluid impermeable, membrane 46 and access opening 44 permit transdermal communication with access chamber 38 by a needle. Closure membrane 46 is adapted to receive a percutaneous needle puncture without leakage from the puncture. Elongated implant body 32, access chamber 38, delivery tube 40, and closure membrane 46 cooperate to provide a fluid impermeable vascular access device 20 which may receive without leakage a medical treatment fluid such as chemotherapy agents, pain medication, and the like.

First end 34 of elongated implant body 32 is generally pointed to provide a means to urge apart the sides of sheath 22 as vascular access device 20 is inserted into the open end of sheath 22 as is more fully described herein. While first end 34 is generally pointed, it does not terminate in a sharp point, but rather tapers down to the diameter of delivery tube 40. In this manner, first end 34 provides a smooth transition between delivery tube 40 and the enlarged diameter of access chamber 38. Preferably, second end 36 is also generally pointed to define parting surfaces or leading edges 48. While leading edges 48 may form a sharp parting edge to second end 36, alternatively, leading edges 48 may define a slightly rounded but still tapered second end 36. Pointed or tapered second end 36 provides vascular access device 20 with the ability to be removed with the same ease with which access device 20 is implanted.

As best seen in FIGS. 1, 2, and 3, elongated implant body 32 of vascular access device 20 includes a low-profile unitary body having a pair of laterally spaced sidewalls 50 and 52, a spanning bottom wall 54, and a top wall 56. Elongated implant body 32 is roughly cylindrical in shape and, preferably, has a length of approximately two and one-quarter inches and a width of approximately between one-quarter and three-eighths inch. Preferably, the length of elongated implant body 32 is between approximately four and seven times the width of implant body 32. The low profile of elongated implant body 32 permits vascular access device 20 to be readily implanted under the skin of the patient.

Bottom wall 54 is preferably flat or otherwise includes flattened regions in order to stabilize vascular access device 20 from rolling over once implanted under the skin of the patient. After vascular access device 20 is implanted, when the outer tissue over implant body 32 is pressed down, flat bottom wall 54 will seat elongated implant body 32 against the bone structure of the patient. The distal edges of top wall 56 form access opening 44 therebetween, in which closure membrane 46 is positioned. Membrane 46 is preferably sealed to the under surface of top wall 56. Alternatively, side walls 50 and 52 include flanges 56a. Membrane 46 may extend and be sealed between top wall 56 and flanges 56a. Sidewalls 50, 52, bottom wall 54, and top wall 56 converge toward tapered first end 34 in order to provide a smooth exterior surface. Furthermore, access chamber 38 tapers down within elongated implant body 32 to the outlet opening 34a provided in first end 34. Treatment fluid contained within access chamber 38, therefore, has a smooth flow transition between access chamber 38 and the interior lumen of delivery tube 40.

Second end 36 preferably includes a laterally extending retrieval aperture 58 defining a curvilinear path 58a through the vascular access device 20. Retrieval aperture 58 is engaged by retrieval tool 26 as described more fully herein in order to remove vascular access device 20 from the patient, such as when vascular access device 20 is no longer needed, when access device 20 needs to be replaced or serviced, or the like. While retrieval aperture 58 preferably extends transversely through second end 36, alternatively, retrieval aperture 58 may extend only partially through second end 36 in order to form an indentation or recess that similarly accommodates a cooperating alternatively configured retrieval tool 26. Preferably, second end 36 includes grooves 60 which extend longitudinally from the distal end of second 36 along the sides of leading edges 48 to retrieval aperture 58. Grooves 60 provide longitudinal guide surfaces for retrieval tool 26 during the selected removal of vascular access device 20 as is hereinafter described in greater detail. Alternatively, retrieval aperture 58 may be drilled or otherwise formed in only one side of second end 36.

An alternative manufacture or assembly of vascular access device 20 is shown in FIG. 3A, and provides a snap-fit construction for an elongated implant body 32'. Elongated implant body 32' has laterally spaced exterior sidewalls 50', 52', and top wall 56'. Access chamber 38' is provided in an insertable, modular housing 62. Modular housing 62 includes a laterally spaced pair of interior sidewalls 64 and an interior bottom wall 66. Closure membrane 46' extends between interior sidewalls 64 and is sealingly secured to the peripheral edges of interior sidewalls 64 in order to define access chamber 38'. Vascular access device 20' is assembled by snapping modular housing 62, with closure membrane 46' extending between interior sidewalls 64, into elongated implant body 32'. Delivery tube 40' is inserted over first end 34' and in communication with hole 34a' and held in place by known connecting means, such as by band clamp 42'. When modular housing 62 is inserted between exterior sidewalls 50, 52, closure membrane 46 is preferably positioned to sealingly engage against the lower interior surfaces defined by top wall 56 about elongated access opening 44'.

In another preferred embodiment of the invention illustrated in FIGS. 5–7, an elongated implant body 132 includes a pair of access chambers 138 and 139. Access chambers 138, 139 are each selectively accessed by access openings 144 and 145, respectively. Elongated access openings 144 and 145 are longitudinally aligned and spaced in a top wall 156. In like manner to the previously described embodiment, elongated implant body 132 includes a generally pointed first end 134 and a generally pointed second end 136. Second end 136 includes a transversely extending retrieval aperture 158 which opens between a first sidewall 150 and a second sidewall 152. Second end 136 also includes a pair of guide grooves 160 which extend longitudinally along leading edges 148 of second end 136. First end 134 is coupled with a delivery tube 140 by known means, such as by a band clamp 142. Delivery tube 140 is positioned to deliver treatment fluids, either simultaneously or separately, from respective access chambers 138 and 139 to the treatment site in the patient.

As best seen in FIGS. 6 and 7, access chambers 138 and 139 are preferably disposed in a stacked relationship within elongated implant body 132. Access chambers 138, 139 are, therefore, generally aligned to extend along a longitudinal axis of elongated implant body 132 to first end 134. Alternatively, access chambers 138, 139 may be disposed in side-by-side relationship internally of elongated implant body 132, but still preferably extending in alignment along the longitudinal axis of elongated implant body 132. Delivery tube 140 includes a first lumen 141 and a second lumen 143 which extend the length of delivery tube 140. First access chamber 138 opens out through first end 134 into first lumen 141 in delivery tube 140. In like manner, second access chamber 139 opens out through first end 134 into second lumen 143 in delivery tube 140. Lumen 141 and lumen 143 are mutually segregated within delivery tube 140 so as to prevent commingling of treatment fluids. With elongated implant body 132, two medications can be applied through the respective membranes 146a and 146b to the treatment site in the patient either simultaneously or separately through use of the two elongated access openings 144, 145.

FIG. 8 illustrates a third preferred embodiment of the present invention, in which a vascular access device 220 includes an elongated implant body 232 with two longitudinally spaced and arrayed access openings 244 and 245. Access openings 244, 245 are located between sidewalls 250 and 252 in a top wall 256. A pair of curved indentations 261 are formed in sidewall 250 in lateral alignment with elongated access openings 244 and 245. Similarly, another pair of arcuate indentations 262 are formed in sidewall 252 in lateral alignment with elongated access openings 244, 245 and laterally opposed from indentations 261. Side indentations 261, 262 assist a medical practitioner in tactilely identifying the precise locations of elongated access openings 244, 245 once vascular access device 220 is implanted. Side indents 261, 262 are also used to tactilely determine the orientation of vascular access device 220 when implanted in the patient. Since side indents 261, 262 are maintained in registry with elongated access openings 244, 245, the medical practitioner may press down on the patient's skin in order to tactilely locate side indents 261, 262 and physically grasp elongated implant body 232. Most preferably, indents 261 are shaped differently than indents 262 in order to assist the medical practitioner in determining the orientation of vascular access device 220 within the patient.

A raised ridge 264 preferably projects from top wall 256 and extends laterally from sidewall 250 to sidewall 252. Raised ridge 264 is located on top wall 256 between access openings 244 and 245. Since raised ridge 264 is maintained in registry relative to the spacing between access openings 244 and 245, raised ridge 264 provides a tactile differentiation structure that indicates the separation between the two access openings 244 and 245. Raised ridge 264 permits a medical practitioner to tactilely differentiate between access openings 244 and 245 in order to ensure that a needle is inserted into the correct access chamber 238, 239.

In manner similar to previous embodiments, elongated implant body 232 provides a first end 234 and a second end 236. Both first end 234 and second end 236 are generally pointed to ease insertion and removal of vascular access device 220 from the patient's body, with second end 236 including a transverse retrieval aperture 258 and pair of guide grooves 260 to accommodate retrieval tool 26.

Elongated implant bodies 32, 32', 132, and 232 are most preferably made from titanium which has not been previously used or reground. Furthermore, it is preferred that the material is free from foreign matter and dye marks, so that the material is compatible for insertion into the patient's body. Alternatively, other medical implant metals and materials may be advantageously employed.

As shown in FIG. 9, flexible sheath 22 includes a tubular body 70. Tubular body 70 includes a narrow distal end 72 and enlarged, wide proximate end 74. Wide proximate end 74 is configured to form an enlarged enclosure region 76 that opens out through wide proximate end 74. Enlarged enclosure 76 is roughly the same configuration as elongated implant body 32. Enlarged enclosure 76 includes a taper 78 that necks down to the overall diameter of the remaining length of tubular body 70 which extends to distal end 72. Tapered transition 78 of enlarged enclosure 76 seats tapered first end 34 of elongated implant body 32 during the implant procedure that is hereinafter described. Tubular body 70 is formed from a flexible material and is provided with opposed tear paths 82 that run the length of tubular body 70.

Tubular body 70 is adapted to tear along tear paths 82. A set of pull tabs 84 connect to wide proximate end 74 and project from opposite sides of tubular body 70. Pull tabs 84 are used for pulling and splitting tubular body 70 along longitudinal tear paths 82 once vascular access device 20 is positioned within the patient as described herein.

Preferably, sheath 22 is made from a polytetrafluoroethylene material. The material has preferably not been previously used or reground, so as to be free from foreign matter and dye marks. These characteristics ensure compatibility for insertion of sheath 22 into the patient. Alternatively, other plastics may be used, such as other self-lubricating plastics, and are preferably formed through an extrusion process.

Sheath 22 and dilator 24 form an introducer assembly. Dilator 24 includes a handle 86 and a shaft 90 which extends from handle 86. Dilator 24 has a configuration complementary to the configuration of sheath 22, although the external dimensions of dilator 24 are roughly equivalent to the dimensions of the internal bore of sheath 22. Shaft 90 has a distal end 92 of relatively small diameter in order to permit its insertion into and through flexible sheath 22 down to sheath narrow distal end 72. Dilator distal end 92 protrudes through the opening of sheath distal end 72 in order to form a hard plastic surface that forms a tunnel when pressure is applied to handle 86. Adjacent dilator handle 86, shaft 90 is expanded into an enlarged lobe 94. Enlarged lobe 94 is configured generally similar to the configuration of elongated implant body 32 and sheath enlarged enclosure 76. Enlarged lobe 94 includes a taper 96 which necks down to the remaining narrower section of shaft 90. Enlarged lobe 94, in cooperation with sheath enlarged enclosure 76, is used to form an enlarged tunnel in the patient's body in order to receive and implant elongated implant body 32. Cooperative dilator taper 96 and sheath taper 78 causes the combination to spread the surrounding tissues of an insertion aperture in the patient through which vascular access device 20 is to be inserted. Extending longitudinally through dilator 24 is a longitudinal bore 98. Bore 98 is used in receiving a guide wire as is hereinafter more fully described. Dilator bore 98 coaxially aligns with the bore through sheath 22 for this guiding function as is described herein.

Retrieval tool 26 includes a handle 300 and a shaft 302 extending from handle 300. Retrieval tool 26 includes a pointed distal end 304 on shaft 302 which operates to separate and dissect tissue as retrieval tool 26 is inserted through an incision in the patient. A hook 306 is located toward distal end 304. As shown in FIG. 9C, a hook 306a is preferably located at the end of an offset neck 307a. Neck 307a is angled complimentary to the taper of second end 36, 136, 236. Hook 306 is therefore offset from a longitudinal axis 302a of the retrieval tool 26 and is configured to insert within retrieval aperture 58, 58', 158, or 258 in elongated implant body 32, 32', 132, or 232. Hook 306 most preferably is formed by a recess in the side of shaft 302 so as to limit the protrusion of hook 306 from the side of shaft 302. In this preferred embodiment, hook 306 is barb-like and minimizes resistance to insertion of retrieval tool 26 into the patient. A sharp guide edge 308 extends from pointed distal end 304 back to hook 306. Sharp guide edge 308 mates with and slides along groove 60, 60', 160, or 260 in second end 36, 36', 136, or 236, or elongated body 32, 32', 132, or 232. Sharp edge 308 and the respective groove, therefore, cooperate in order to guide hook 306 into the respective retrieval aperture during the removal procedure.

Figure 10:
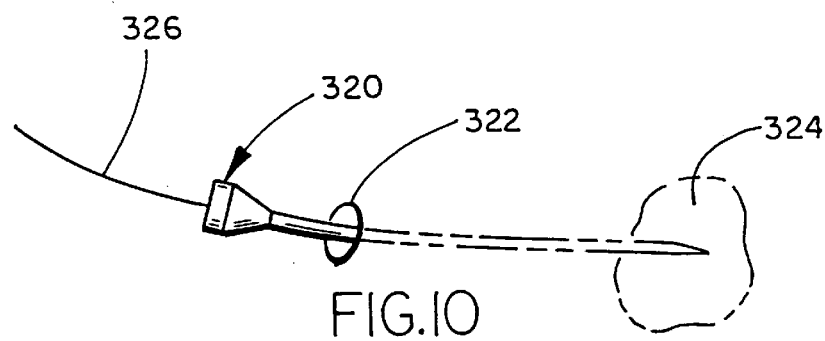
FIG. 10 is a perspective view of a conventional guide wire being inserted through an introducer needle into a first location in the body extending to a site of application.
Figures 11A, 11B:
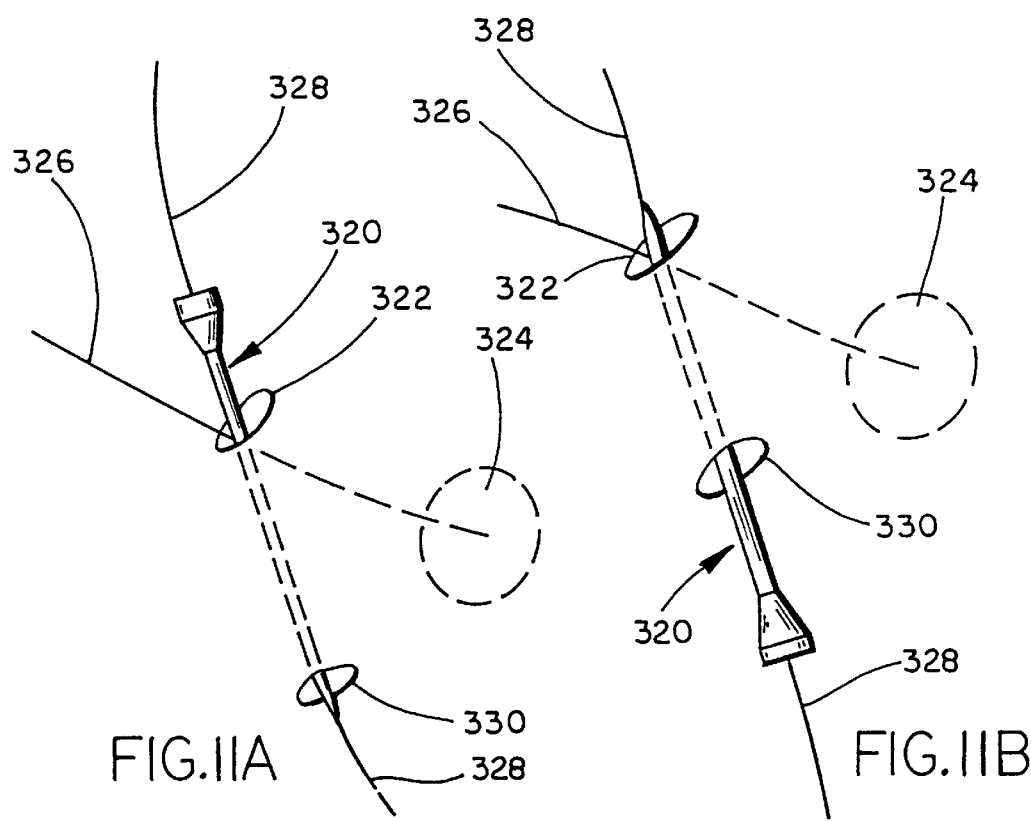
FIG. 11A is a perspective view of a second guide wire being installed through the first location in the body and extending externally from the body through the second location.
FIG. 11B is a perspective view of a second guide wire being installed through a second location in the body and extending externally from the body through the first location.

As best seen in FIG. 10, in the preferred method of implanting vascular access device 20, an introducer needle 320 is inserted into the body of the patient at a first location in order to form a first or body access hole 322. Needle 320 is extended to a preselected treatment site, such as an organ or vein 324 inside the patient's body, where a medicine or nutritional solution is to be delivered. A first or body access guide wire 326 is fed through needle 320 in order to position the end of guide wire 326 at treatment site 324. Needle 320 is removed, leaving guide wire 326 in position within the patient, protruding from opening 322 and leading to treatment site 324. Referring to FIGS. 11A and 11B, a second or tunnel guide wire 328 is introduced into the patient. Tunnel guide wire 328 is inserted through use of an introducer needle 320. Preferably, introducer needle 320 is inserted to form a tunnel hole 330 in the patient at a second site removed from opening 322, and is used to direct tunnel guide wire 328 through the patient and back out original opening 322 (FIG. 11B). Alternatively, tunnel guide wire can be inserted through original body access opening 322 and then exited through tunnel opening 330 (FIG. 11A). It should be noted that both holes 322 and 330 are relatively small and may or may not require stitches after completion of the procedure. With needle 320 removed, tunnel guide wire 328 forms a second path through the patient's body and protrudes at both ends through both holes 322 and 330.

As seen in FIG. 12, after tunnel guide wire 328 is inserted, dilator 24 is used to force and guide flexible sheath 22 down along tunnel guide wire 328. Narrow distal end 72 of sheath 22 is first inserted through second hole 330 and forced along guide wire 328. Dilator 24 and guide wire 328 are used to extend sheath 22 through the patient such that sheath distal end 72 protrudes externally through body access hole 322 at the first location. Dilator enlarged lobe 94 is used to force sheath enlarged enclosure 76 through tunnel hole 330, with tapers 96 and 78 spreading tissue as sheath enlarged enclosure 76 is inserted. In some instances, it may be preferable to make one or more small incisions at tunnel hole 330 in order to assist in the dilation of the hole and accommodate sheath enlarged enclosure 76.

Once sheath 22 is in place in the body of the patient with distal end 72 protruding from body access hole 322 and enlarged enclosure 76 implanted, sheath proximate end 74 opens out through tunnel hole 330 with pull tabs 84 located external of the patient's body. Dilator 24 is removed, and sheath 22 is left in place to define a vascular access tunnel with enlarged enclosure 76 opening through tunnel hole 330. Vascular access device 20 is inserted into open proximate end 74 of sheath 22. Delivery tube 40 is first inserted into sheath 22, and is thus guided through tunnel hole 330 until delivery tube 40 emerges through body access hole 322. Elongated implant body 32 is forced through tunnel hole 330 by way of sheath enlarged enclosure 76, with generally pointed first end 34 operating to separate tissue during insertion. Elongated implant body 32 is inserted until it is seated within the patient's body in enlarged enclosure 76.

As seen in FIG. 13, when vascular access device 20 is submerged below the skin and delivery tube 40 extends externally at body access hole 322, sheath pull tabs 84 are pulled apart, causing sheath 22 to split longitudinally along tear paths 82 while sliding over vascular access device 20 and exiting back through tunnel hole 330. Once vascular access device 20 is thus placed and sheath 22 removed, tunnel opening 330 may be stitched closed (FIG. 14). In some instances, stitches may not be required for closure of tunnel opening 330. Preferably, a needle is inserted through sealing membrane 46 of vascular access device 20, and access chamber 38 and delivery tube 40 are flushed with a solution such as a saline solution. This flushing procedure is used to assure that there is no air left in vascular access device 20 prior to further insertion of delivery tube 40.

Figure 15:
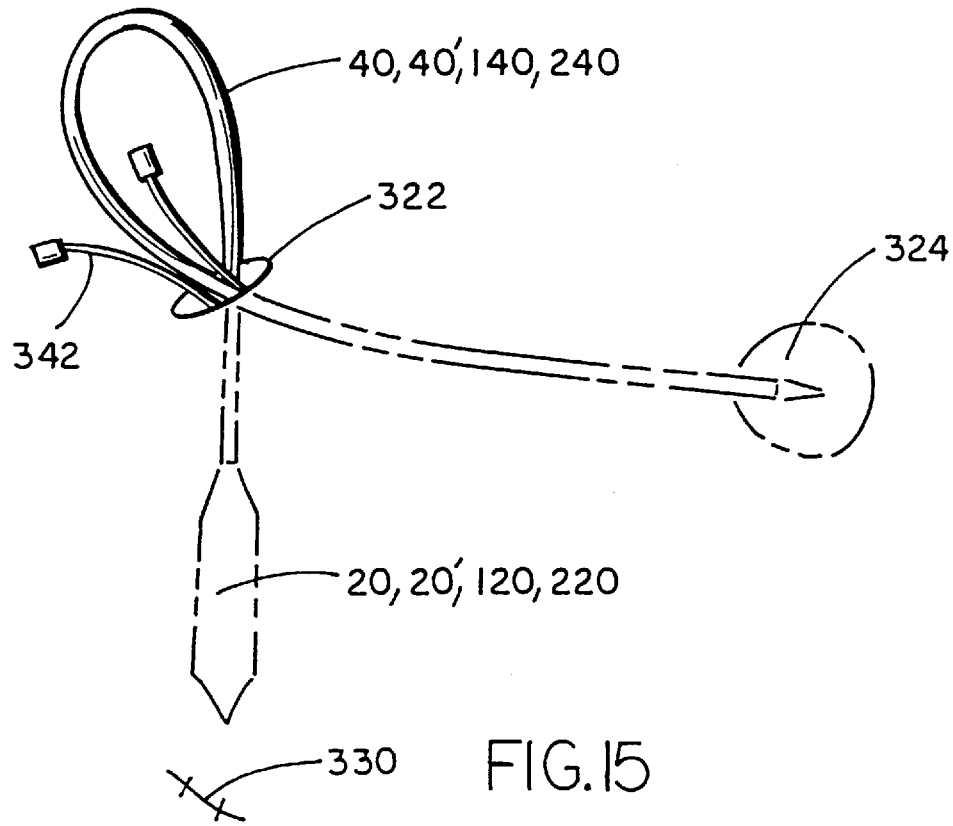
FIG. 15 is a perspective view of the present invention installed in the body and having the delivery tube of the vascular access device extending to the conventional sheath to the application site in the body.
Figure 16:
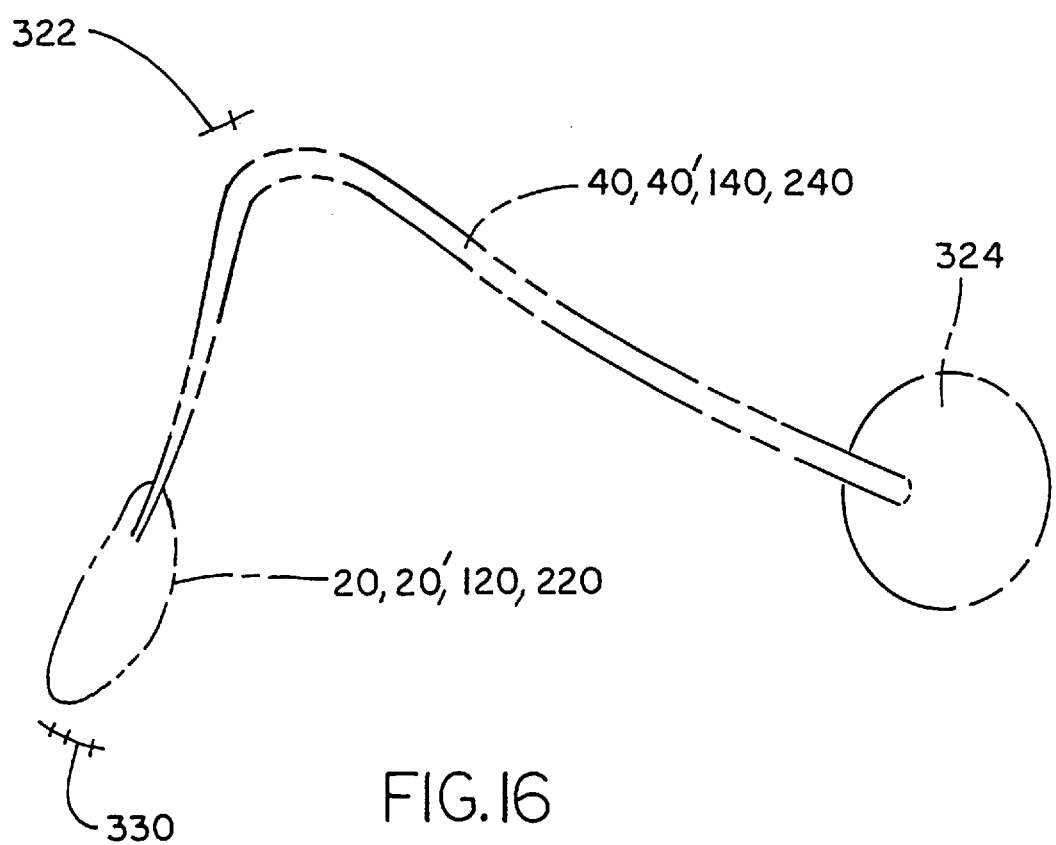
FIG. 16 is a perspective view of the present invention installed and the delivery tube subcutaneously implanted with both entrance locations in the body being closed.
Figure 17:
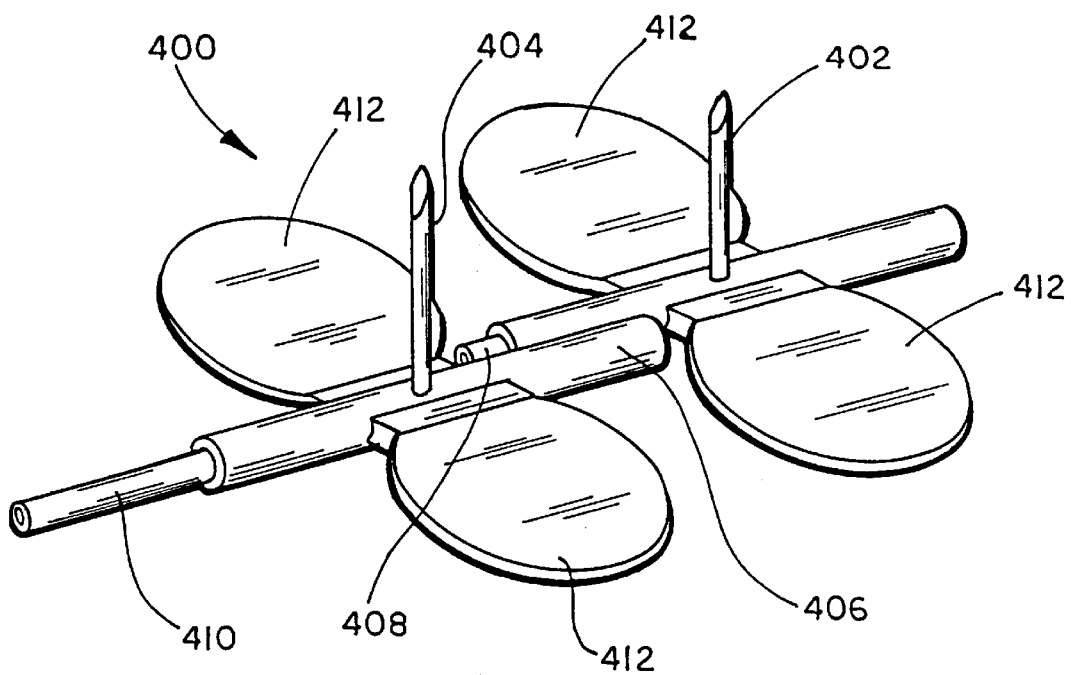
FIG. 17 is a perspective view of a needle assembly of the present invention.
Figure 18:
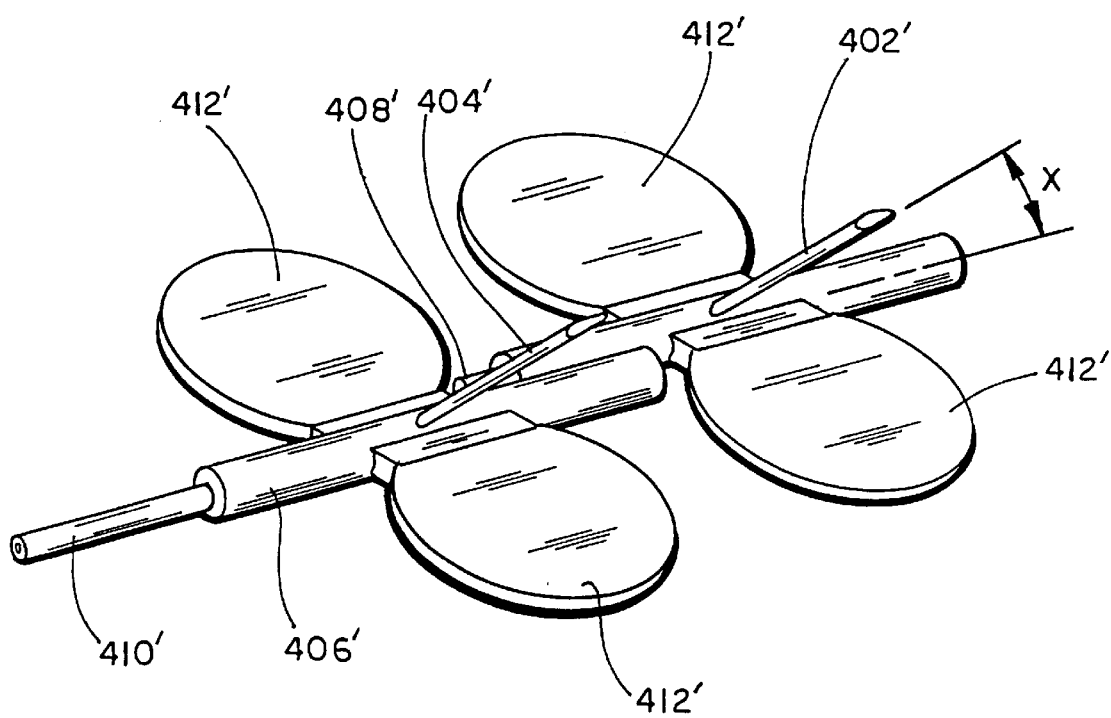
FIG. 18 is a perspective view of a second embodiment of the needle assembly of the present invention.

Again referring to FIG. 14, a dilator 340 and sheath 342 of conventional configuration are inserted through body access opening 322 and guided down the protruding body access guide wire 326. Tear-away sheath 342 is thus directed to treatment site 324 within the patient's body. Once tear-away sheath 342 is so positioned, dilator 340 and body access guide wire 326 are removed from the patient. Referring to FIG. 15, the protruding free end of delivery tube 40 is directed back into body access opening 322, but is inserted down the protruding open end of sheath 342. Delivery tube 40 is directed down sheath 342 until the distal end of delivery tube 40 is positioned at treatment site 324. Sheath 342 is removed by tearing the separable portions and withdrawing sheath 342 back through body access opening 322. Referring to FIG. 16, the small protruding loop or bend of delivery tube 40 which is left protruding body access opening 322 is then tucked through hole 322 beneath the skin, so that vascular access device 20 is completely implanted beneath the skin. Generally, body access hole 322 is sufficiently small that a closure stitch is not required. However, body access opening 322 may be stitched closed as necessary. Tunnel hole 330 may be closed or sutured as necessary, particularly if an incision had been used to extend or enlarge tunnel 330.

In this manner, all of vascular access device 20 is subcutaneously implanted in the body of the patient. Vascular access device 20 may receive medication transdermally through a needle to deliver the medication to the desired location in the body. The risk of overall infection with vascular access device 20 is far less than externally extending catheters, and the procedure to implant the vascular access device of the present invention is far less invasive than conventional vascular ports. Implant of vascular access device 20 may be performed in this manner under local anesthesia and pursuant to outpatient procedures. Preferably, vascular access device 20 may be implanted in approximately fifteen to twenty minutes.

In describing the preferred method, the terms "first" and "second" are used herein in order to distinguish between different elements. While the preferred method is described in a sequential manner, this sequential description and the terms "first" and "second" are not intended to limit to the preferred sequence so described. The terms "first" and "second" are, therefore, not intended to be limiting as to the sequence of the method or priority in which the different elements are utilized. For example, in the preferred method, dilator 24 is described as being used to insert sheath 22 prior to the insertion of sheath 342. Alternatively, dilator 340 may be used to insert sheath 342 to treatment site 324 prior to the insertion of sheath 22. One skilled in the art will recognize other alternatives from the description herein.

In order to remove vascular access device 20, an incision is made near or at the original site of tunnel hole 330. Retrieval tool 26 is inserted at the incision point, with pointed distal end 304 entering the incision. In order to latch onto vascular access device 20, 20', 120, or 220, the vascular access device is physically held by the respective sidewalls of the device through the patient's skin, and preferably by side indents 260, 262. Hook 306 is guided along groove 60, 60', 160, or 260 in order to direct hook 306 into retrieval aperture 58, 58', 158, or 258. Pointed distal end 304 dissects tissues as retrieval tool 26 is inserted. Once hook 306 is engaged in the respective retrieval aperture, retrieval tool 26 is withdrawn in order to remove vascular access device 20, 20', 120, or 220 from beneath the patient's skin. Tapered second end 36, 36', 136, or 236 of the vascular access device allow the vascular access device to be withdrawn with minimal damage to the surrounding tissue.

A needle assembly 400 which may be used in conjunction with dual access chambers 138, 139 and 238, 239 includes a pair of noncoring needles 402 and 404. Needles 402, 404 are mounted on a tubular body 406. Tubular body 406 is generally formed from a relatively hard plastic or similar material, in order to maintain needles 402 and 404 in spaced registry. Tubular body 406 is coupled with a pair of fluid administration tubes 408, 410. Tubes 408, 410 extend from tubular body 406 generally perpendicular relative to needles 402, 404. Tubes 408, 410 are coupled through tubular body 406 to needles 402 and 404, respectively, so as to transmit fluid in a mutually exclusive manner to needles 402, 404. Needles 402, 404, tubular body 406, and tubes 408, 410, therefore, form a fluid-tight communication. Needles 402, 404 are spaced complementary to the spacing of access openings 144, 145 and 244, 245. Tubular body 406 maintains needles 402, 404 in this proper registry while being inserted into the vascular access device and while in an inserted condition.

Noncoring needles 402 and 404 include longitudinally extending lumens which extend through tubular body 406 to the distal end portions of the needles. The distal portions of the needles are angled such that each needle can be inserted into a septum or membrane without making a hole in the septum and, therefore, no leakage will occur at the puncture site. Tubular body 406 is provided with two pair of relatively pliable arms 412, which attach to opposed sides of tubular body 406. Alternatively, tubular body 406 may be provided with a single pair of pliable arms 412, in which case arms 412 are used to commonly insert both needles 402, 404. Since arms 412 are relatively pliable, arms 412 may be bent to provide a grip for needle assembly 400. Once needles 402, 404 are inserted into the respective access chambers 138, 139 or 238, 239, arms 412 are released and provide stabilizers for needles 402, 404. Arms 412 thus resist the shifting of needles 402, 404 when inserted into the appropriate vascular access device.

In another preferred embodiment of the needle assembly, a pair of needles 402' and 404' are extended from tubular body 406' at an acute angle. Most preferably, the acute angle of needles 402', 404' relative to tubes 408', 410' is approximately 30°. In this alternative embodiment of needle assembly 400', the needles do not extend outwardly as far as would an orthogonal needle, which is particularly suitable for pediatric surgery in which the dimensions of the patient and the patient's body parts are generally smaller.

While dual-needle assembly 400 is preferably used with a vascular access device of the present invention, dual-needle assembly 400 may alternatively be used advantageously with other dual-chambered vascular access systems, such as a dual-access port. In such use, tubular body 406 maintains a spacing between needles 402, 404 that is in registry with the spacing of two port access openings in the port.

The profile of vascular access device 20 of the present invention is small so that it can be inserted just below the skin. The elongated access opening 44, 44', 144 and 145, or 244 and 245 to access the respective chamber in the device eases the insertion of a needle or needles through the respective membranes, 46, 46', 146a, 146b, 246a, or 246b. The enlarged and elongated access openings accommodate a wide variation in the angle of attack of the needle being inserted, and permit a needle having an acute angle with respect to the longitudinal access of the respective tube, all of which eases the comfort level of the device, especially for children or small adults. The identifying indentations on the sides of vascular device 220 provide for tactile recognition of device 220 and the proper orientation of vascular access device 220 within the patient.

It can be seen that the present invention may be provided in a kit which includes a combination of dilator 24, sheath 22, and any one of vascular access devices 20, 20', 120, and 220. Furthermore, retrieval tool 26 and/or needle assembly 400 may be included in the kit.

It should be understood from the foregoing that the vascular access device as disclosed herein may be used for chronic venous or organ access. The implanted device facilitates repeated intermittent infusions of chemotherapeutic agents, medicines, such as those drugs used for therapy, nutritional fluids, blood products as well as blood sampling. A sheath introduction eases the placement of the device and reduces access site trauma to the vein, organ, or other location in the body to which the medicine or therapy is to be applied. Furthermore, as the access device includes an elongated shape having first and second generally pointed ends, the insertion and removal of the device is far simpler than the prior known portal devices and yet provides the same advantages of the portal devices, but eliminates the need for the extensive surgery that is required with prior known portal devices. Furthermore, the vascular access device of the present invention offers the advantages of the conventional externally extending catheter but with reduced risk of infection as the device does not extend externally of the body. The dual-chamber vascular access device provides two separate infusion chambers with unitary body to facilitate intermittent infusion of chemotherapeutic agents, drugs for therapy or blood sampling, and more particularly to infuse any incompatible fluids.

While the preferred embodiment is described in terms of a human patient, the invention may also be used with an animal patient as well. Further, the invention may alternatively be used to introduce treatment materials other than fluids into the patient, such as, for example, a wire lead or other type of implant.

It is to be understood that the foregoing is a description of the preferred embodiments. One skilled in the art will recognize that variations, modifications, and improvements may be made without departing from the spirit of the invention disclosed herein. The scope of the protection afforded is to be measured by the claims which follow and the breadth of interpretation which the law allows.

I claim:

1. A vascular access device for inserting into the body of a patient, said vascular access device adapted to be used for periodic delivery of medical treatment to a preselected location in the body of the patient, such as delivery of a fluid to a treatment site, said vascular access device comprising:

an elongated implant body having a top wall, a bottom wall, opposed side walls, a first end, a closed second end, and at least one access chamber formed therein, said first end defining a first opening in communication with said access chamber, and said top wall defining a second opening in communication with said access chamber, said elongated implant body having a width and a length greater than said implant body width, said top wall, said side walls, and said bottom walls converging to form said first and second ends of said implant body, at least said first end being generally pointed an amount sufficient to ease insertion of said elongated implant body through an incision formed in the skin of the patient and generally pointed an amount sufficient to separate tissue during the insertion, and said second end including a retrieval surface for engaging a cooperating structure on a retrieval device whereby engagement between the retrieval device and the retrieval surface permits remote removal of said vascular access device from the body of the patient;

a tubular member having at least one lumen extending therethrough, said tubular member connected to said first end of said elongated implant body, said lumen in fluid communication with said access chamber through said first opening for delivery of material from said access chamber along said tubular member to the preselected location in the body; and a membrane sealing said elongated implant body second opening, said membrane adapted to receive a percutaneous needle puncture without leakage from the puncture, whereby said elongated implant body is adapted to be implanted through an incision which will accommodate said width of said elongated implant body but is less than said length thereof.

2. A vascular access device according to claim 1, wherein said first end of said elongated implant body tapers to said tubular member to provide a smooth transition between said tubular member and said elongated implant body to ease insertion of the elongated implant body into the passage.

3. A vascular access device according to claim 1, wherein said second opening is an elongated opening extending longitudinally along said elongated implant body.

4. A vascular access device according to claim 1, wherein said elongated implant body has a lower surface and an upper surface, said lower surface having a generally planar region so as to reduce rotation of said elongated implant body when implanted, and said second opening is disposed in said upper surface.

5. A vascular access device according to claim 4, further comprising a tactile identification structure disposed on said elongated implant body in preselected registry with said second opening, whereby when implanted said tactile identification structure is used to tactilely locate said second opening.

6. A vascular access device according to claim 5, wherein said elongated implant body has longitudinal sides between said upper surface and said lower surface, said elongated implant body including one of recesses and protrusions disposed on said longitudinal sides in lateral alignment with said second opening, and said tactile identification structure comprises said one of recesses and protrusions.

7. A vascular access device according to claim 1, wherein said access chamber is a first access chamber, said tubular member with said lumen is a first tubular member with a first lumen, and membrane is a first membrane, and further comprising:

a second access chamber formed in said elongated implant body, said elongated implant body defining a third opening and a fourth opening, each of said third and fourth openings in communication with said second access chamber;

a second tubular member with a second lumen extending therethrough, said second tubular member connected to said elongated implant body with said second lumen in fluid communication with said second access chamber through said third openings;

a second membrane sealing said fourth opening, said second membrane adapted to receive a percutaneous needle puncture without leakage from the puncture.

8. A vascular access device according to claim 7, wherein said elongated implant body includes a tactile differentiation structure disposed thereon in registry with said second opening and said fourth opening, whereby when said elongated implant body is implanted, said tactile differentiation structure is used to tactilely locate and differentiate said second opening and said fourth opening.

9. A vascular access device according to claim 8, wherein said tactile differentiation structure comprises a raised surface disposed between said second opening and said fourth opening.

10. A vascular access device according to claim 1, wherein said retrieval surface is provided by one of a recess and a transverse aperture for engaging the cooperating structure on the retrieval device, with the retrieval device being inserted into the body of the patient through an incision remote from said access device.

11. A vascular access device according to claim 10, wherein said second end of said elongated body includes one of a transverse opening and a recess defining said structure for engaging the cooperating structure of the retrieval device.

12. A vascular access device for inserting into the body of a patient said vascular access device adapted to be used for periodic delivery of medical treatment to a preselected location in the body of the patient, such as delivery of a fluid to a treatment site, said vascular access device comprising:

an elongated implant body having a wall, a first end, a second end, and at least one access chamber formed therein, said first end defining a first opening in communication with said access chamber, and said wall defining a second opening in communication with said access chamber, said elongated implant body having a width and a length greater than said implant body width;

a tubular member having at least one lumen extending therethrough, said tubular member connected to said first end of said elongated implant body, said lumen in fluid communication with said access chamber through said first opening for delivery of material from said access chamber along said tubular member to the preselected location in the body; and a membrane sealing said elongated implant body second opening, said membrane adapted to receive a percutaneous needle puncture without leakage from the puncture, whereby said elongated implant body is adapted to be implanted through an incision which will accommodate said width of said elongated implant body but is less than said length thereof, and said second end being generally pointed in an amount sufficient to ease removal of said elongated body from the body of the patient and including a receiving structure adapted for engaging a cooperating structure of a retrieval device.

13. A vascular access device according to claim 12, wherein said receiving structure comprises an indent.

14. A vascular access device according to claim 13, wherein said indent is defined by a withdrawal aperture extending transversely of said second end of said elongated implant body.

15. A vascular access device according to claim 14, wherein said second end includes a groove adjacent said withdrawal aperture for guiding the cooperating structure of the retrieval device into to said aperture.

16. A vascular access device according to claim 15, wherein said second end includes a distal end, said groove extending from said distal end longitudinally of said elongated body to said withdrawal aperture.

17. A vascular access device according to claim 12, wherein said first end is generally pointed in an amount sufficient to ease insertion of said elongated implant body into a passage formed in the body of the patient.

18. A vascular access device according to claim 12, further comprising a tactile identification structure disposed on said elongated implant body in preselected registry with said second opening, whereby when implanted said tactile identification structure is used to tactilely locate said second opening.

19. A vascular access device according to claim 18, wherein said elongated implant body has an upper surface and a lower surface and longitudinal sides between said upper surface and said lower surface, said elongated implant body including one of recesses and protrusions disposed on said longitudinal sides in lateral alignment with said second opening, and said tactile identification structure comprises said one of recesses and protrusions.

20. A vascular access device according to claim 12, wherein said access chamber is a first access chamber, said tubular member with said lumen is a first tubular member with a first lumen, and membrane is a first membrane, and further comprising:

a second access chamber formed in said elongated implant body, said elongated implant body defining a third opening and a fourth opening, each of said third and fourth openings in communication with said second access chamber;

a second tubular member with a second lumen extending therethrough, said second tubular member connected to said elongated implant body with said second lumen in fluid communication with said second access chamber through said third opening;

a second membrane sealing said fourth opening, said second membrane adapted to receive a percutaneous needle puncture without leakage from the puncture.

21. A vascular access device for inserting into a passage in the body of a patient, said vascular access device for delivering medical treatment to a preselected location in the body of the patient, said vascular access device comprising:

an elongated body having a closed end, an open end, a wall extending therebetween, and at least a first access chamber formed therein for receiving the medical treatment, said first access chamber in fluid communication with said open end, said elongated body further including an elongated access opening in said wall, said elongated access opening being longitudinally aligned with said elongated body and in fluid communication with said access chamber, said elongated body further having a length to width ratio of at least about four to one to minimize the size of incision required in the body for insertion of said vascular access device, said open end being adapted to separate tissue when said elongated body is inserted into an incision formed in the skin of the patient, said closed end being adapted to separate tissue when said elongated body is removed through an incision formed in the skin of the patient, and said elongated body including a retrieval structure for engaging a cooperating structure on a retrieval device whereby engagement between said retrieval structure and the retrieval device permits removal of said vascular access device from the body of the patient;

a catheter tube having a first lumen extending therethrough, said catheter tube coupled to said open end of said elongated body, said first lumen of said catheter tube in fluid communication with said first access chamber of said elongated body for delivering the medical treatment from said first access chamber of said elongated body to the preselected location in the body, said open end of said elongated body defining an insertion end; and a membrane sealing said elongated access opening, said membrane adapted to receive a percutaneous needle puncture without leakage from the puncture.

22. A vascular access device according to claim 21, said wall of said elongated body tapering to said open and closed ends of said elongated body to ease insertion and removal of the elongated body through an incision formed in the skin of the patient.

23. A vascular access device according to claim 21, wherein said closed end includes said retrieval structure for engaging the cooperating structure of the retrieval device whereby said vascular access device can be removed from the body of the patient with the retrieval device.

24. A vascular access device according to claim 21, wherein said open end is generally pointed to ease insertion of said vascular access device through an incision in the body of the patient.

25. A vascular access device according to claim 24, wherein said closed end of said vascular access device is generally pointed to ease removal of said vascular access device through the incision in the body of the patient.

26. A vascular access device for inserting and implanting into a passage in the body of a patient, said vascular access device for delivering medical treatment to a preselected location in the body of the patient, said vascular access device comprising:

an elongated body having a closed end, an open end, a wall extending therebetween, at least a first access chamber formed therein for receiving the medical treatment, said access chamber in fluid communication with said open end, and an elongated access opening in said wall, said elongated access opening longitudinally aligned with said elongated body and in fluid communication with said access chamber, said closed end of said elongated including a retrieval surface for cooperating with a retrieval device so that said vascular access can be removed from the body of the patient with the retrieval device, with the retrieval device being inserted through an incision in the body of the patient remote from the vascular access device;

a catheter tube having a first lumen extending therethrough, said catheter tube coupled to said open end of said elongated body, said first lumen of said catheter tube in fluid communication with said first access chamber of said elongated body for delivering the medical treatment from said first access chamber of said elongated body to the preselected location in the body, and a membrane sealing said elongated access opening, said membrane adapted to receive a percutaneous needle puncture without leakage from the puncture.

27. A vascular access device according to claim 26, wherein said elongated body includes a second access chamber therein and in fluid communication with said open end, said open end having a pair of adjacent openings, said tubular member having a second lumen extending therethrough, said first access chamber of said elongated body in fluid communication with said first lumen of said tubular member through one of said adjacent openings, said second access chamber of said elongated body in fluid communication with said second lumen of said tubular member through the other of said adjacent openings.

28. A vascular access device according to claim 26, wherein said open end is generally pointed to ease insertion of said elongated body into the body of the patient and sufficiently pointed to separate tissue during the insertion of said elongated body into the body of the patient.

29. A vascular access device according to claim 28, wherein said second end is generally pointed to ease removal of said elongated body from the body of the patient and sufficiently pointed to separate tissue during the removal of said elongated body from the body of the patient.

30. A vascular access device for inserting into a passage in the body of a patient, said vascular access device for delivering medical treatment to a preselected location in the body of the patient said vascular access device comprising:

an elongated body having a closed end, an open end, a wall extending therebetween, at least a first access chamber formed therein for receiving the medical treatment, said access chamber in fluid communication with said open end, and an elongated access opening in said wall, said elongated access opening longitudinally aligned with said elongated body and in fluid communication with said access chamber, said wall of said elongated body tapering to said open and closed ends of said elongated body, and said open and closed ends being generally pointed to ease insertion and removal of said elongated body trough an incision formed in the skin of the patient and further being sufficiently pointed an amount sufficient to separate tissue when inserted or removed through the incision and said elongated body including a retrieval structure for cooperating with a cooperating structure of a retrieval device whereby registration between the retrieval device and the elongated body permits remote removal of said vascular access device from the body of the patient;

a catheter tube having a first lumen extending therethrough, said catheter tube coupled to said open end of said elongated body, said first lumen of said catheter tube in fluid communication with said first access chamber of said elongated body for delivering the medical treatment from said fist access chamber of said elongated body to the preselected location in the body; and a membrane sealing said elongated access opening, said membrane adapted to receive a percutaneous needle puncture without leakage from the puncture.

31. A vascular access device for inserting and implanting into a passage in the body of a patient, said vascular access device for delivering medical treatment to a preselected location in the body of the patient, said vascular access device comprising:

an elongated body having a closed end, an open end, a wall extending therebetween, at least a first access chamber formed therein for receiving the medical treatment, said access chamber in fluid communication with said open end, and an elongated access opening in said wall, said elongated access opening longitudinally aligned with said elongated body and in fluid communication with said access chamber, said wall of said elongated body tapering to said open and closed ends of said elongated body to ease insertion of the elongated body into a passage formed in the patient, and said open and closed ends being generally pointed to ease insertion and removal of said elongated body from the passage in the patient, and said closed end including a retrieval aperture extending transversely of said closed end of said elongated body for registering with a cooperating structure on a retrieval tool;

a catheter tube having a first lumen extending therethrough, said catheter tube coupled to said open end of said elongated body, said first lumen of said catheter tube in fluid communication with said first access chamber of said elongated body for delivering the medical treatment from said first access chamber of said elongated body to the preselected location in the body; and a membrane sealing said elongated access opening, said membrane adapted to receive a percutaneous needle puncture without leakage from the puncture.

32. A vascular access device according to claim 31, wherein said closed end includes a distal end and a groove extending from said distal end longitudinally of said elongated body to said aperture.

33. A vascular access device for inserting into the body of a patient, said vascular access device adapted to be used for periodic delivery of medical treatment to a preselected location in the body of the patient, such as delivery of a fluid to a treatment site, said vascular access device comprising:

an elongated implant body having a top wall, a bottom wall, opposed side walls, a first end, a closed second end, and at least one access chamber formed therein, said first end defining a first opening in communication with said access chamber, and said top wall defining a second opening in communication with said access chamber, said elongated implant body having a width and a length greater than said implant body width, said top wall, said side walls, and said bottom walls converging to form said first and second ends of said implant body, at least said first end being generally pointed an amount sufficient to ease insertion of said elongated implant body into a passage formed in the body of the patient, said elongated body including an indent for engaging the cooperating structure of the retrieval device;

a tubular member having at least one lumen extending therethrough, said tubular member connected to said first end of said elongated implant body, said lumen in fluid communication with said access chamber through said first opening for delivery of material from said access chamber along said tubular member to the preselected location in the body; and a membrane sealing said elongated implant body second opening, said membrane adapted to receive a percutaneous needle puncture without leakage from the puncture, whereby said elongated implant body is adapted to be implanted through an incision which will accommodate said width of said elongated implant body but is less than said length thereof.

34. A vascular access device for inserting into the body of a patient, said vascular access device adapted to be used for periodic delivery of medical treatment to a preselected location in the body of the patient, such as delivery of a fluid to a treatment site, said vascular access device comprising:

an elongated implant body having a wall, a distal end, a proximal end, and at least one access chamber formed in said body, said proximal end including a first opening in communication with said access chamber, said wall including a second opening in communication with said access chamber, and said proximal end defining an insertion end and being generally pointed an amount sufficient to ease insertion of said elongated body into a passage formed on the body of the patient and, further, being pointed an amount sufficient to separate tissue when said elongated implant body is inserted into the body of the patient, and said elongated implant body including a retrieval structure for registering with a cooperating structure of a retrieval device whereby registration of the retrieval device and said structure permits removal of said vascular access device;

a tubular member having at least one lumen extending therethrough, said tubular member coupled to said proximal end of said elongated body, said lumen being in communication with said access chamber through said first opening for delivery of material from said access chamber along said tubular member to the preselected location in the body; and a membrane sealing said elongated implant body second opening, said membrane adapted to receive a percutaneous needle puncture without leakage from the puncture.

35. A vascular access device according to claim 34, wherein said second end of said elongated body is generally pointed in an amount sufficient to ease removal of said elongated body from the passage formed in the body of the patient.

36. A vascular access device according to claim 34, wherein said retrieval structure comprises a recess for engaging the cooperating structure of the retrieval device.

37. A vascular access device according to claim 34, wherein said elongated body has a length to width ratio of at least about four to one to minimize the size of an incision required in the body for insertion of said vascular access device.

* * * * *

UNITED STATES PATENT AND TRADEMARK OFFICE
CERTIFICATE OF CORRECTION

PATENT NO. : 5,919,160
DATED : July 6, 1999
INVENTOR(S) : Dominic Joseph Sanfilippo, II It is certified that error appears in the above-identified patent and that said Letters Patent is hereby corrected as shown below:

Column 3,
Line 24, delete -- ; -- after "access"

Column 14,
Line 64, "openings" should be -- opening --

Column 15,
Line 24, insert -- , -- after "patient"

Column 17,
Line 54, "," should be -- ; -- after "body"

Column 18,
Line 14, insert -- , -- after "patient"
Line 26, "trough" should be -- through --
Line 29, insert -- , -- after "incision"

Column 19,
Line 35, "the" should be -- a -- in the first instance
Line 35, "the" should be -- a -- in the second instance Signed and Sealed this Twenty-seventh Day of November, 2001

*Attest:*

*Attesting Officer*

NICHOLAS P. GODICI
*Acting Director of the United States Patent and Trademark Office*